United States Patent [19]

Canela

[11] Patent Number: 5,690,621
[45] Date of Patent: Nov. 25, 1997

[54] DRAINABLE POUCH FOR COLOSTOMY PATIENTS

[76] Inventor: Heriberto Canela, 8027 W. 14th Ave., Hialeah, Fla. 33014

[21] Appl. No.: 622,723

[22] Filed: Mar. 26, 1996

[51] Int. Cl.$^6$ ................................................ A61F 5/44
[52] U.S. Cl. ................................................ 604/333
[58] Field of Search ................................ 604/277, 278, 604/332–340

[56] References Cited

U.S. PATENT DOCUMENTS

| | | | |
|---|---|---|---|
| 2,638,898 | 5/1953 | Perry | 604/340 |
| 4,411,659 | 10/1983 | Jenson et al. | 604/340 |
| 4,451,258 | 5/1984 | Jensen | 604/333 |
| 4,516,974 | 5/1985 | Davis | 604/333 |
| 5,248,308 | 9/1993 | von Emster | 604/332 |
| 5,470,325 | 11/1995 | Fundock | 604/332 |

*Primary Examiner*—Robert A. Clarke
*Attorney, Agent, or Firm*—J. Sanchelima

[57] ABSTRACT

A drainable pouch for colostomy patients with a stoma and that includes a valve for selectively releasing the gases trapped within the pouch. The valve assembly is removably mounted permitting a user to rinse the interior of the pouch from the uppermost portion. The valve also contains an odor suppresant filter that may include an impregnated fragrance. A cap member is used to cover the outlet spout. A sheet having cooperative dimensions and made out of a non-transparent material is used to conceal said pouch from public view.

2 Claims, 2 Drawing Sheets

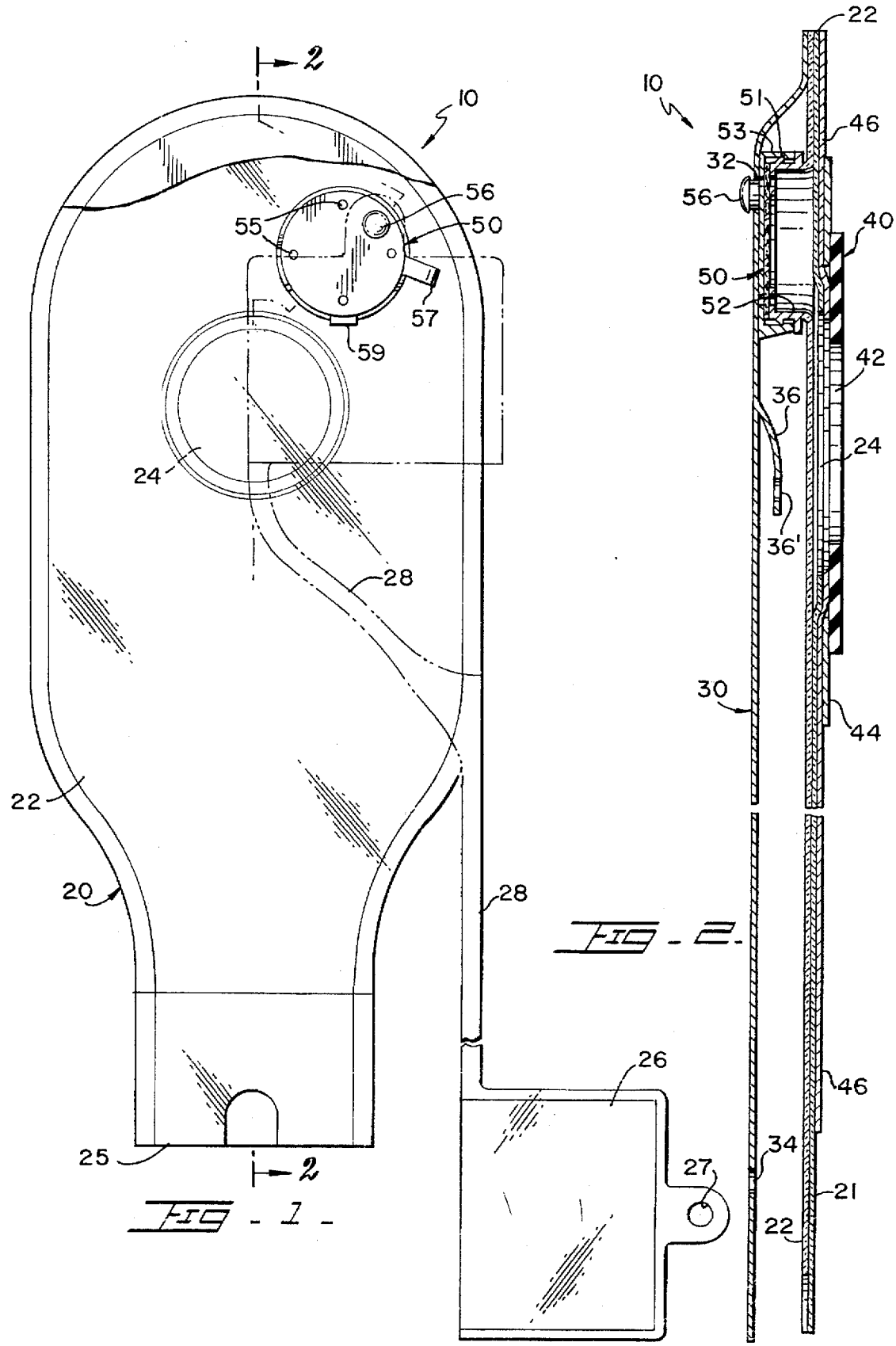

DRAINABLE POUCH FOR COLOSTOMY PATIENTS

BACKGROUND OF THE INVENTION

1. Field of the Invention

The present invention relates to a drainable pouch for colostomy patients, and more particularly, to the type that includes a escape gas valve and a protective cap for the pouch outlet spout.

2. Description of the Related Art

Several designs of drainable pouch for colostomy patients exist in the market, however none of them disclose the features included in the present invention. The drainable pouch claimed in the present application overcomes some of the shortcomings present in the existing pouches, such as the inconvenience of having a practically sealed pouch that does not have any outlet, orifice, vent or breathing port that allows a user to selectively permit the gas to escape from the pouch while a user is carrying it. The present invention overcomes this shortcoming providing a valve mounted in the pouch that permits a user to selectively free the gas accumulated as the result of the excrement and the valve also includes a fragrance impregnated filter. Another inconvenience frequently encountered by colostomy patients in their daily use of pouches is that the cleaning procedure is uncomfortable having to rinse the pouch with water through the pouch tail, in the lower portion thereof, requiring a user to bend in an uncomfortable position. In contrast, the present invention discloses an opening located in the uppermost portion of the pouch through which the water flows rinsing the pouch. The water is then drained through the lower pouch outlet spout by gravity. Finally, a protective cap covers the pouch tail thus avoiding any possible escape of odor or direct contact with excrement particles left in the pouch tail after the interior of the pouch was rinsed.

SUMMARY OF THE INVENTION

It is one of the main objects of the present invention to provide a drainable pouch that has a valve assembly that permits a user to selectively release the gas contained in the pouch through an odor-removal or fragrance impregnated filter.

It is another object of this invention to provide a drainable pouch that has a removable valve assembly that permits a user to rinse the pouch from the uppermost portion cleansing the entire pouch body and draining the contents through a drawing outlet spout in the lowermost portion without requiring a user to be in an uncomfortable position.

It is another object of the present invention to provide a drainable pouch that includes a protective cap member for covering the pouch outlet spout.

It is still another object of the present invention to provide a drainable pouch that includes a plastic cover sheet made out of a non-transparent material that conceals the pouch from public sight.

It is yet another object of this invention to provide such a device that is cost effective to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 is a elevational front view of the drainable pouch with the valve assembly and a protective cap attached to the pouch by a strap.

FIG. 2 is a cross section of the present invention shown in the previous figure taken along line 2—2.

DETAILED DESCRIPTION OF THE PREFERRED EMBODIMENT

Figure 3:
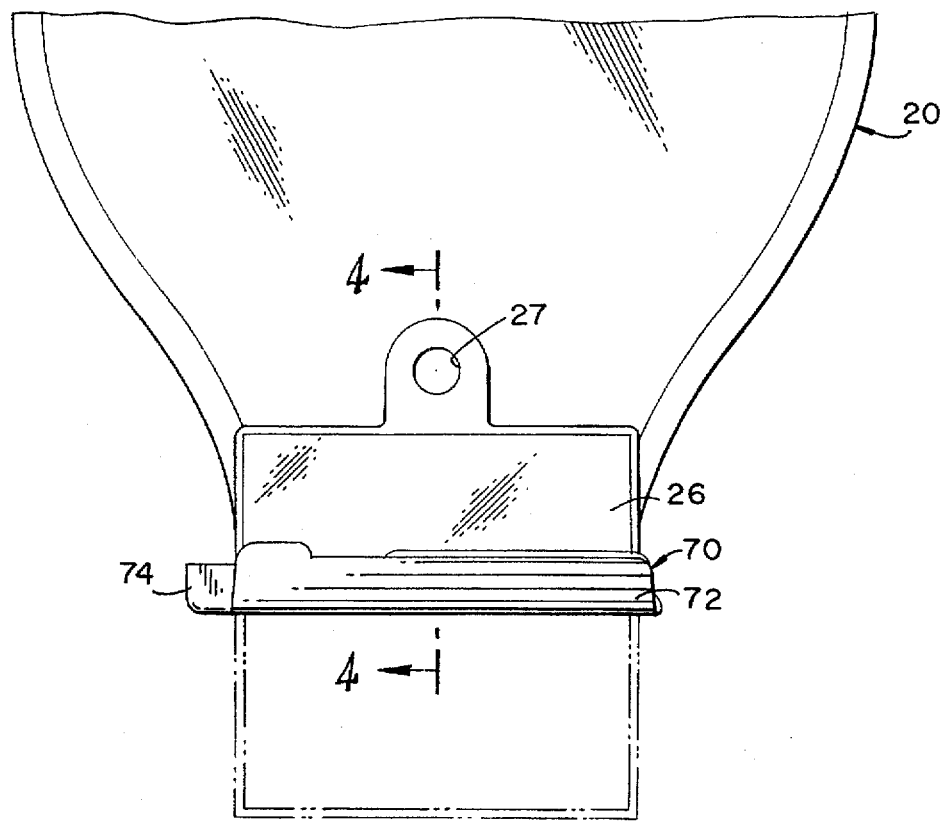
FIG. 3 is a partial front view of the lower portion of the pouch with the pouch tail folded and held in place by a locking mechanism. The unfolded pouch tail is shown in phantom.

Referring now to the drawings, where the present invention is generally referred to with numeral 10, it can be observed that it basically includes drainable pouch 20, cover sheet 30, adhesive disk frame 40, valve assembly 50 and clamp assembly 70.

Drainable pouch 20, as most common pouches used by colostomy patients, has a longitudinal shape and includes stoma opening 24 located at the center of the uppermost portion of pouch 20. Stoma opening 42 of adhesive disk frame 40 is in coaxial alignment with opening 24. Outlet spout 25 is located at the lowermost portion of pouch 20. Drainable pouch 20, as shown in FIGS. 1 and 2, comprises rear wall 21 and front wall 22.

Adhesive disk frame 40 is rigidly mounted to rear wall 21 in the periphery of stoma opening 24 of pouch 20. Adhesive film 44 as well as adhesive frame 40, when device 10 will be applied, are adhered to a user's peristomal skin accommodating disk stoma opening 42 to the user's stoma (not shown), which can be of any desired size and shape.

Figure 5:
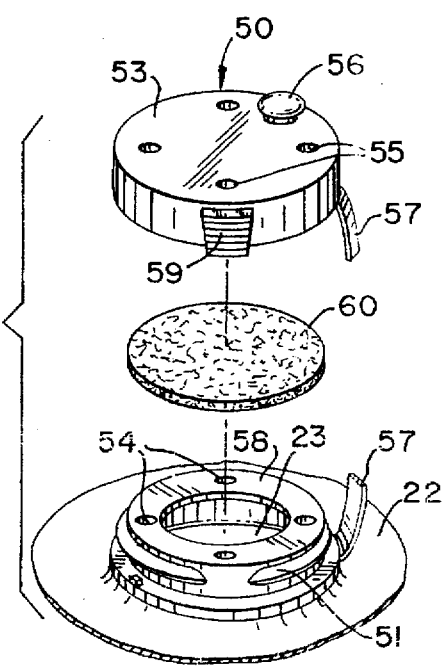
FIG. 5 is an exploded view of the removable valve assembly.

In FIGS. 1; 2 and 5 valve assembly 50 is peripherally mounted to aperture 23 of front wall 22 of pouch 20. Valve assembly 50 basically includes threaded neck 52 with four breathing orifices 54, cap member 53 with four breathing orifices 55 and filter member 60. Cap member 53 is connected to threaded neck 52 by connecting members 62. Threaded neck 52 is rigidly mounted to aperture 23 of front wall 22. In the preferred embodiment, threaded neck 52 has single thread 51, stop member 57 and four breathing orifices 54 located at its uppermost surface 58. On the other hand, cap member 53 includes four breathing orifices 55, lid 59 mounted to outer periphery of cap member 53 and protuberance 56 mounted on the top surface. Cap member 53 is removably mounted to threaded neck 52 sandwiching filter member 60, as best seen in FIG. 5. Valve assembly 50 is designed to permit a user to release the air and gas contained in pouch 20 by rotating cap member 53 and breathing orifices 55 coincide with breathing orifices 54. A user applies a smooth pressure over walls 21 and 22 causing the release of air and gas, thereby reducing the occupied volume inside pouch 20. Filter member 60, in the preferred embodiment, is designed to remove odor escaping from pouch 20. Filter member 60 can be made out of a odor absorbent material or impregnated with a pleasant fragrance.

Figure 4:
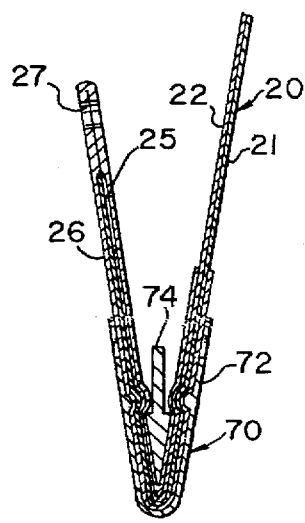
FIG. 4 is a detail elevational partial cross section of the previous figure taken along line 4—4.

Drainable pouch 20 has a lower tail that ends with outlet spout 25. When a user uses device 10, she or he folds outlet spout 25 and sealing it with a locking mechanism. The locking mechanism could be clamp assembly 70, as best seen in FIGS. 3 and 4. Pouch outlet spout 25 is folded over case member 74 and the raised bar member 72 is pressed until the latter snaps in place and is securely closed.

When a user needs to eliminate the human excrement and clean pouch 20, cap guiding member 53 is removed by pulling out lid 59 and filter member 60. Opening 23 serves as the passage for the rinsing water. Clamp assembly 70 is removed and the rinsing water injected through upper opening 23 bars the content of pouch 20 out.

Pocket or cap member 26 is attached to pouch 20 through connecting strap 28. When the hygienic process is finished, pocket 26 covers outlet spout 25. In this manner, the still wet end is covered avoiding any contact with the user's clothing. Eyelet 27 of pocket 26 is designed to permits the user to hook pocket 20 to protuberance 56 of guiding cap member 53 while the hygiene process is occurring, as best seen in FIGS. 1 and 3.

Cover sheet 30 conceals device 10 from public sight and has upper opening 32 which receives protuberance 56 to keep sheet 30 in place and away from interfering with the user. When a user rinses pouch 20, cover sheet 30 is rolled up and is held in place by strap member 36 received by protuberance 56 through opening 36'. In this manner, the user can manipulate pouch 20 without the interference of cover sheet 30. Also, lower opening 34 is designed to be received by protuberance 56 once cover sheet 30 is folded.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A pouch for colostomy patients with a stoma, and said pouch has an elongated shape with first and second ends, said first end including an outlet spout and further including an opening adjacent to said second end, and further including a disk with a central opening that is coaxially aligned with said opening and said disk being mounted to said pouch and removably attached to the periphery of said stoma, and said pouch comprising:

A) valve means mounted to said pouch to permit a user to selectively release any gases trapped within said pouch wherein said valve means is removably mounted thereby permitting a user to rinse said pouch by flushing it with water passing from the opening of said removed valve means and out through said outlet spout and wherein said valve means includes filter means for treating said escaping gas, said filter means is impregnated with a fragrance;

B) a cap member for selectively covering said outlet spout;

C) an opaque sheet member attached to said second end and having cooperative dimensions to conseal said pouch;

D) a clamp assembly for removably holding and sealing said folded first end and cap member in place.

2. A pouch for colostomy patients with a stoma, and said pouch has an elongated shape with first and second ends, said first end including an outlet spout and further including an opening adjacent to said second end, and further including a disk with a central opening that is coaxially aligned with said opening and said disk being mounted to said pouch and removably attached to the periphery of said stoma, and said pouch comprising:

A) valve means mounted to said pouch to permit a user to selectively release any gases trapped within said pouch wherein said valve means is removably mounted thereby permitting a user to rinse said pouch by flushing it with water passing from the opening of said removed valve means and out through said outlet spout and wherein said valve means includes filter means for treating said escaping gas, said filter means is impregnated with a flagrance, wherein said valve means includes a threaded neck member connecting the interior of said pouch and a cap member rotably mounted over said threaded neck member, said threaded neck and cap members including each cooperative through openings that can be selectively aligned to open or close the connection through said threaded neck member to the interior of said pouch;

B) a cap member for selectively covering said outlet spout;

C) an opaque sheet member attached to said second end and having cooperative dimensions to conseal said pouch;

D) a clamp assembly for removably holding and sealing said folded first end and cap member in place.

\* \* \* \* \*